US006759244B2

(12) United States Patent
Alikani et al.

(10) Patent No.: US 6,759,244 B2
(45) Date of Patent: Jul. 6, 2004

(54) COMPOSITE BLASTOCYSTS (CBS) FROM AGGREGATES OF DISSOCIATED CELLS OF NON-VIABLE PRE-EMBRYOS

(75) Inventors: Mina Alikani, New York, NY (US); Steen Malte Willadsen, Windermere, FL (US)

(73) Assignee: Art Institute of New York and New Jersey, Inc., New York, NY (US)

(*) Notice: Subject to any disclaimer, the term of this patent is extended or adjusted under 35 U.S.C. 154(b) by 97 days.

(21) Appl. No.: 10/036,581

(22) Filed: Nov. 8, 2001

(65) Prior Publication Data

US 2003/0087431 A1 May 8, 2003

(51) Int. Cl.$^7$ .......................... C12N 5/00; C12N 5/02; C12N 5/08; C12N 5/10; A61K 35/44
(52) U.S. Cl. .................. 435/373; 435/366; 435/363; 424/582
(58) Field of Search ............................ 435/373, 366, 435/363; 424/582

(56) References Cited

U.S. PATENT DOCUMENTS

| | | | |
|---|---|---|---|
| 5,061,620 A | 10/1991 | Tsukamoto et al. | 435/7 |
| 5,166,065 A | 11/1992 | Williams et al. | 435/325 |
| 5,340,740 A | 8/1994 | Petitte et al. | 435/325 |
| 5,449,620 A | 9/1995 | Khillan | 435/325 |
| 5,453,357 A | 9/1995 | Hogan | 435/7 |
| 5,523,226 A | 6/1996 | Wheeler | 435/325 |
| 5,541,081 A | 7/1996 | Hardy et al. | 435/24 |
| 5,589,376 A | 12/1996 | Anderson et al. | 435/325 |
| 5,591,625 A | 1/1997 | Gerson et al. | 435/325 |
| 5,635,386 A | 6/1997 | Palsson et al. | 435/372 |
| 5,843,780 A | 12/1998 | Thomson | 435/363 |
| 5,914,268 A | 6/1999 | Keller et al. | 435/325 |
| 6,132,952 A | 10/2000 | Cohen et al. | 435/2 |
| 6,200,806 B1 | 3/2001 | Thomson | 435/366 |
| 6,280,718 B1 | 8/2001 | Kaufman et al. | 435/363 |

FOREIGN PATENT DOCUMENTS

| | | |
|---|---|---|
| WO | 94/03585 | 2/1994 |
| WO | 98/07841 | 2/1998 |
| WO | 00/32140 | 11/1998 |
| WO | 00/0012682 | 3/2000 |
| WO | 01/0134776 | 5/2001 |
| WO | 01/0162899 | 8/2001 |

OTHER PUBLICATIONS

Nagy, A., 1993, PNAS, vol. 90, pp. 8424–8428.*
Luo, J. , 1997, Nature, vol. 388, pp. 778–782.*
The American H ritage® Dictionary of th English Lanugage; http://www.bartleby.com/61/75/P0517550.html.*
Biotech Lifescience Dictionary, http://biotech.icmb.utex-as.edu/search/dict-search.phtml?title=pre-embryo.*

National Institutes of Health Guidelines for Research Using Human Pluripotent Stem Cells. National Institutes of Health, www.nih.gov/news/stemcell/stemcellguidelines.htm, pp. 1–13, Nov. 1, 2000, 65 FR 69951.
Fletcher L. US Stem cell policy comes under fire. Nature Biotechnology, 19: 893–894, 2001.
Tarkowski AK and Wroblewska J. Development of blastomeres of mouse eggs isolated at the 4– and 8–cell stage J Embryology and Experimental morphology, 18(1): 155–80, 1967.
Willadsen SM. Cloning of sheep and cow embryos. Genome, 31(2):956–962, 1989.
Willadsen SM. Nuclear transplantation in sheep embryos. Nature, 320:63–65, 1986.
Fehilly CB, Willadsen SM. Embryo manipulation in farm animals. Oxf Rev Reprod Biol., 8: 379–413, 1986.
Fehilly CB, Willadsen SM, Dain AR, Tucker EM. Cytogenetic and blood group studies of sheep/goat chimaeras. J Reprod Fertil., 74(1): 215–21, 1985.
Willadsen SM, Godke RA. A simple procedure for the production of identical sheep twins. Vet Rec., 114(10): 240–3, 1984.
Fehilly CB, Willadsen SM, Tucker EM. Interspecific chimaerism between sheep and goat. Nature. Feb. 16–22, 1984;307(5952):634–6.
Fehilly CB, Willadsen SM, Tucker EM. Experimental chimaerism in sheep. J Reprod Fertil., 70(1):347–51, 1984.
Willadsen SM. The development capacity of blastomeres from 4– and 8–cell sheep embryos. J Embryol Exp Morphol., 65:165–72, 1981.
Willadsen SM, Polge C. Attempts to produce monozygotic quadruplets in cattle by blastomere separation. Vet Rec., 108(10): 211–3, 1981.
Willadsen SM. The viability of early cleavage stages containing half the normal number of blastomeres in the sheep. J Reprod Fertil., 59(2):357–62, 1980.

(List continued on next page.)

Primary Examiner—Peter Paras
Assistant Examiner—Valarie Bertoglio

(57) ABSTRACT

A preparation and a method of making composite blastocysts (CBs) from aggregates of dissociated cells of non-viable pre-embryos are disclosed. The CB is characterized morphologically by having two distinct tissue types, the inner cell mass (ICM) and the trophectoderm (TE), and a blastocoelic cavity (BC). The method of making CBs is an aggregation process (AP) comprising inter alia the following steps: 1) dissociation of discarded pre-embryos; 2) isolation of single nucleated cells from dissociated discarded pre-embryos; 3) microsurgical encapsulation of several cells within a host zona pellucida or artificial aggregation with or without a non-zona vessel; and 5) primary culture of the cell aggregates for multiplication and differentiation of cells. One particularly advantageous embodiment is that the starting material is non-viable pre-embryos. Another advantageous embodiment is that the AP allows individual cells from non-viable pre-embryos to further multiply, and become integrated into CBs. The novel CBs and the novel aggregation process disclosed.

1 Claim, 5 Drawing Sheets

OTHER PUBLICATIONS

Figure 1:
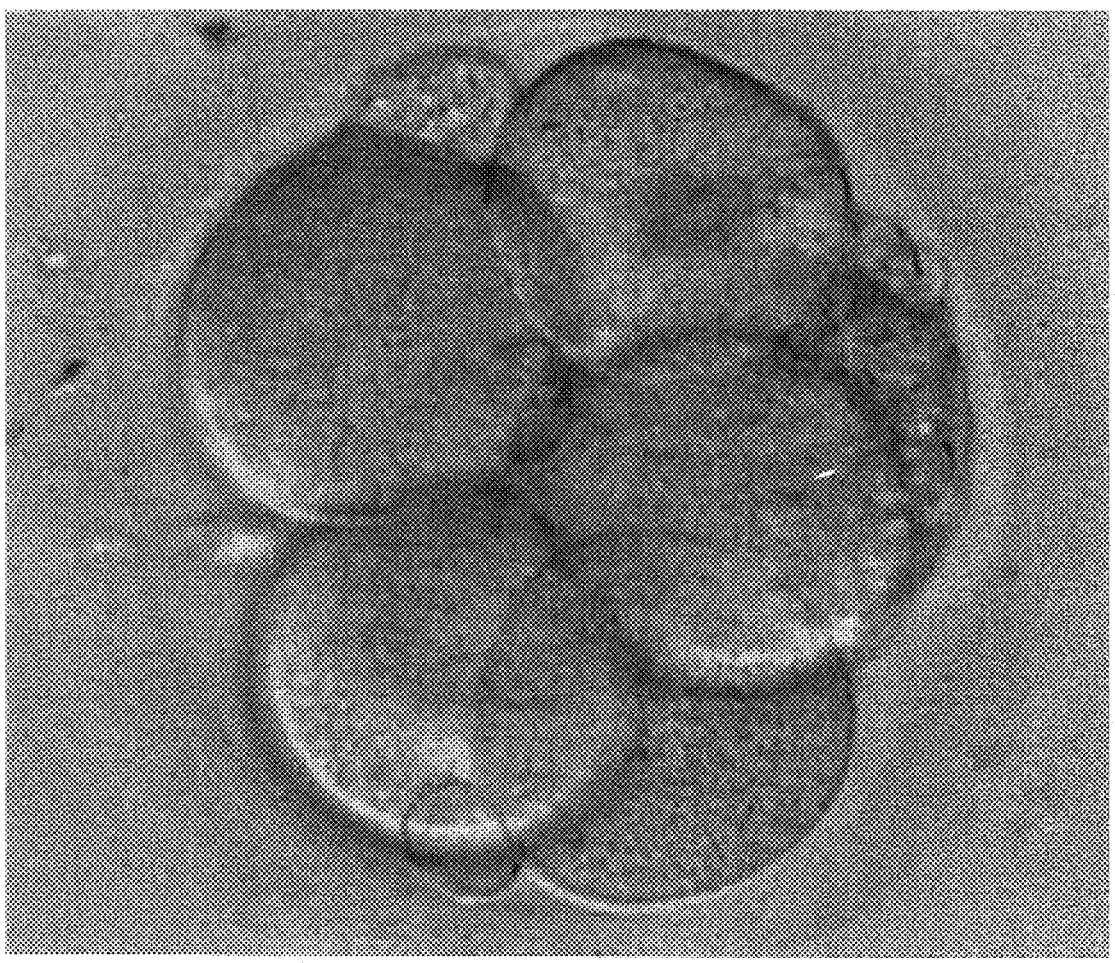
Figure 2:
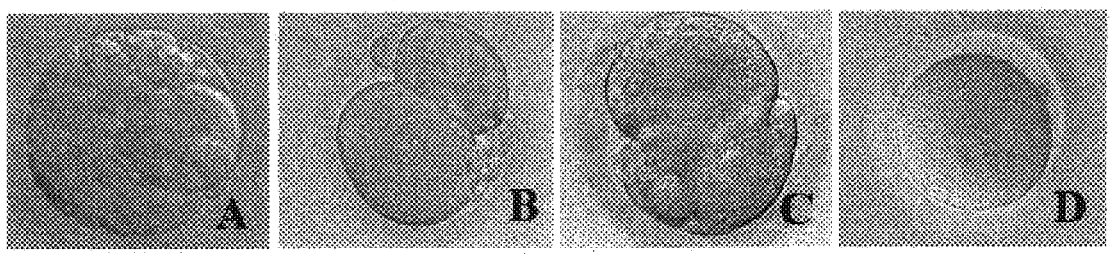

Willadsen SM. A method for culture of micromanipulated sheep embryos and its use to produce monozygotic twins. Nature, 277:298–300, 1979.

Barritt J, Willadsen S, Brenner C, Cohen J. Cytoplasmic transfer in assisted reproduction. Hum Reprod Update. Jul.–Aug. 2001;7(4):428–35.

Willadsen S, Levron J, Munne S, Schimmel T, Marquez C, Scott R, Cohen J. Rapid visualization of metaphase chromosomes in single human blastomeres after fusion with in–vitro matured bovine eggs. Hum Reprod. Feb. 1999;14(2):470–5.

Levron J, Willadsen SM, Shimmel T, Cohen J. Cryopreservation of activated mouse oocytes and zygote reconstitution after thaw. Hum Reprod. Dec. 1998;13 Suppl 4:109–16.

Sandalinas M, Sadowy S, Alikani M, Calderon G, Cohen J, Munne S. Developmental ability of chromosomally abnormal human embryos to develop to the blastocyst stage. Hum Reprod. Sep. 2001;16(9):1954–8.

Alikani M, Calderon G, Tomkin G, Garrisi J, Kokot M, Cohen J. Cleavage anomalies in early human embryos and survival after prolonged culture in–vitro. Hum Reprod., 15(12):2634–43, 2000.

Cao W, Brenner CA, Alikani M, Cohen J, Warner CM. Search for a human homologue of the mouse Ped gene. Mol Hum Reprod., 5(6):541–7, 1999.

Alikani M, Cohen J, Tomkin G, Garrisi GJ, Mack C, Scott RT. Human embryo fragmentation in vitro and its implications for pregnancy and implantation. Fertil Steril., 71(5):836–42, 1999.

Warner CM, Cao W, Exley GE, McElhinny AS, Alikani M, Cohen J, Scott RT, Brenner CA. Genetic regulation of egg and embryo survival. Hum Reprod., 13 Suppl 3:178–90; discussion 191–6, 1998.

Cohen J, Alikani M, Garrisi JG, Willadsen S. Micromanipulation of human gametes and embryos: ooplasmic donation at fertilization. Hum Reprod Update. Mar.–Apr. 1998;4(2):195–6.

Munne S, Marquez C, Reing A, Garrisi J, Alikani M. Chromosome abnormalities in embryos obtained after conventional in vitro fertilization and intracytoplasmic sperm injection. Fertil Steril. May 1998;69(5):904–8.

Cohen J, Scott R, Alikani M, Schimmel T, Munne S, Levron J, Wu L, Brenner C, Warner C, Willadsen S. Ooplasmic transfer in mature human oocytes. Mol Hum Reprod. Mar. 1998;4(3):269–80.

Kligman I, Benadiva C, Alikani M, Munne S. The presence of multinucleated blastomeres in human embryos is correlated with chromosomal abnormalities. Hum Reprod. Jul. 1996;11(7):1492–8.

Alikani M, Palermo G, Adler A, Bertoli M, Blake M, Cohen J. Intracytoplasmic sperm injection in dysmorphic human oocytes. Zygote. Nov. 1995;3(4):283–8.

Munne S, Alikani M, Tomkin G, Grifo J, Cohen J. Embryo morphology, developmental rates, and maternal age are correlated with chromosome abnormalities. Fertil Steril. Aug. 1995;64(2):382–91.

Alikani M, Cohen J, Palermo GD. Enhancement of fertilization by micromanipulation. Curr Opin Obstet Gynecol. Jun. 1995;7(3):182–7.

Sultan KM, Munne S, Palermo GD, Alikani M, Cohen J. Chromosomal status of uni–pronuclear human zygotes following in–vitro fertilization and intracytoplasmic sperm injection. Hum Reprod. Jan. 1995;10(1):132–6.

Alikani M, Noyes N, Cohen J, Rosenwaks Z. Monozygotic twinning in the human is associated with the zona pellucida architecture. Hum Reprod. Jul. 1994;9(7):1318–21.

Grifo JA, Tang YX, Munne S, Alikani M, Cohen J, Rosenwaks Z. Health deliveries from biopsied human embryos. Hum Reprod. May 1994;9(5):912–6.

Cohen J, Alikani M, Liu HC, Rosenwaks Z. Rescue of human embryos by micromanipulation. Baillieres Clin Obstet Gynaecol. Mar. 1994;8(1):95–116. Review.

Munne S, Alikani M, Cohen J. Monospermic polyploidy and atypical embryo morphology. Hum Reprod. Mar. 1994;9(3):506–10.

Cohen J, Schattman G, Suzman M, Adler A, Alikani M, Rosenwaks Z. Micromanipulating human gametes. Reprod Fertil Dev. 1994;6(1):69–81; discussion 81–3.

Liu HC, Cohen J, Alikani M, Noyes N, Rosenwaks Z. Assisted hatching facilitates earlier implantation. Fertil Steril. Nov. 1993;60(5):871–5.

Alikani M, Olivennes F, Cohen J. Microsurgical correction of partially degenerate mouse embyros promotes hatching and restores their viability. Hum Reprod. Oct. 1993;8(10):1723–8.

Alikani M. Micromanipulation of human gametes for assisted fertilization. Curr Opin Obstet Gynecol. Oct. 1993;5(5):594–9. Review.

Neev J, Gonzalez A, Licciardi F, Alikani M, Tadir Y, Berns M, Cohen J. Opening of the mouse zona pellucida by laser without a micromanipulator. Hum Reprod. Jun. 1993;8(6):939–44.

Alikani M, Cohen J. Micromanipulation of cleaved embryos cultured in protein–free medium: a mouse model for assisted hatching. J Exp Zool. Oct. 1, 1992;263(4):458–63.

Cohen J, Alikani M, Reing AM, Ferrara TA, Trowbridge J, Tucker M. Selective assisted hatching of human embryos. Ann Acad Med Singapore. Jul. 1992;21(4):565–70.

Cohen J, Alikani M, Trowbridge J, Rosenwaks Z. Implantation enhancement by selective assisted hatching using zona drilling of human embryos with poor prognosis. Hum Reprod. May 1992;7(5):685–91.

Cohen J, Alikani M, Malter HE, Adler A, Talansky BE, Rosenwaks Z. Partial zona dissection or subzonal sperm insertion: microsurgical fertilization alternatives based on evaluation of sperm and embryo morphology. Fertil Steril. Oct. 1991;56(4):696–706.

Pike IL, Alikani M. Time–dependent loss of developmental potential when two–celled mouse embryos were retained in culture in excised oviducts. Ann N Y Acad Sci. 1988;541:419–23.

Cohen J, Gilligan A, Willadsen S. Culture and quality control of embryos. Hum Reprod. Jun. 1998;13 Suppl 3:137–44; discussion 145–7.

Cohen J, Scott R, Schimmel T, Levron J, Willadsen S. Birth of infant after transfer of anucleate donor oocyte cytoplasm into recipient eggs. Lancet. Jul. 19, 1997;350(9072):186–7.

Levron J, Willadsen S, Bertoli M, Cohen J. The development of mouse zygotes after fusion with synchronous and asynchronous cytoplasm. Hum Reprod. Jun. 1996;11(6):1287–92.

Levron J, Willadsen S, Munne S, Cohen J. Formation of male pronuclei in partitioned human oocytes. Biol Reprod. Jul. 1995;53(1):209–13.

Levron J, Munne S, Willadsen S, Rosenwaks Z, Cohen J. Male and female genomes associated in a single pronucleus in human zygotes. Biol Reprod. Mar. 1995;52(3):653–7.

Cohen J., Malter, C Fehilly, G Wright, C Elsner, H Kort, J Massey (1988) Implantation of embryos after partial opening of the oocyte zona pellucida to facilitate sperm penetration. Lancet, 1988 ii:162.

Cohen J, HE Malter, C Elsner, H Kort, J Massey, MP Mayer (1989) Partial zona dissection of human oocytes when failure of zona pellucida penetration is anticipated. Hum Reprod 4:435–442.

Malter HE, J Cohen (1989) Partial zona dissection of the human oocyte: a nontraumatic method using micromanipulation to assist zona pellucida penetration. Fertil Steril 51:139–148.

Malter HE, J Cohen (1989) Embryonic development after microsurgical repair of polyspermic human zygotes. Fertil Steril 52:373–380.

Malter HE, J Cohen (1989) Blastocyst formation and hatching in vitro following zona drilling of mouse and human embryos. Gamete Res 24:67–80.

Cohen J, C Elsner, H Kort, H Malter, J. Massey, MP Maye, K Wiemer (1990) Impairment of the hatching process following IVF in the human and improvement of implantation by assisting hatching using micromanipulation. Hum Reprod 5:7–13.

Wiker S, H Malter, G Wright, J Cohen (1990) Recognition of paternal pronuclei in human zygotes. J In Vitro Fertil Emb Transfer 7:33–37.

J.Nicos and R.L. Gardner Heterogeneous differentiation of external cells in individual isolated mouse inner cell masses in culture. Embryol. Exp. Morphol.; 80:225–240,1984.

Andrews, P. et al. Cell lines from human germ cell tumours. Teratocarcinoms and Embryonic Stem Cells; A Practical Approach, Oxford: IRL Press, Ch. 8:207–248 (1987).

Andrews, P., et al. Pluripotent Embryonal Carcinoma Clones Derived from the Human Teratocarcinoma Cell Line Tera–2. Lab. Invest., 50(2):147–162 (1984).

Bongso, A., et al., Isolation and culture of inner cell mass cells from human blastocysts Human Reprod., 9(1):2110–2117 (1994).

Bongso, A., et al., "The Growth of Inner Cell Mass Cells from Human Blastocysts," Theriogenology, 41:167 (1994).

Doetschman, T., et al. Establishment Of Hamster Blastocyst–Derived Embryonic Stem (ES) Cells Developmental Biology, 127:224–227 (1988).

Doetschman, T., et al. The in vitro development of blastocyst–derived embryonic stem cell lines: formation of visceral yolk sac, blood islands and myocardium, J. Embryol. Exp. Morph., 87:27–45 (1985).

Evans, M., et al. Establishment in culture of pluripotential cells from mouse embryos, Nature, 292:154–156 (1981).

Notarianni, E., et al. Maintenance and differentiation in culture of pluripotential embryonic cell lines from pig blastocysts. J. Reprod. Fert. Suppl., 41:51–56 (1990).

Notarianni, E., et al. Derivation Of Pluripotent, Emryonic Cell Lines From The Pig And Sheep. J. Rep. & Fert. 43 255–260 (1991).

Piedrahita, et al., On The Isolation Of Embryonic Stem Cells: Comparative Behavior Of Murine, Porcine And Ovine Embryos Theriogenology, 34(5):879–901 (1990).

Rossant, J., et al. The relationahip between embryonic, embryonal carcinoma and embryo–derived stem cells. Cell Diff., 15:155–161 (1984).

Seshagiri, P., et al. Non–Surgical Uterine Flushing for the Recovery of Preimplantation Embryos in Rhesus Monkeys: Lack of Seasonal Infertility. Am. J. Primatol., 29:81–91 (1993).

Strojek, R. et al. A Method For Cultivating Morphologically Undifferentiated Embryonic Stem Cells From Porcine Blastocysts. Theriogenology 33 901–913 (1990).

Sukoyan, M., et al. Isolation and Cultivation of Blastocyst–derived Stem Cell Lines from American Mink (*Mustela vision*) Mol. Reprod. Dev., 33:418–431 (1992).

Sukoyan, M., et al. Embryonic Stem Cells Derived from Morulae, Inner Cell Mass, and Blastocysts of Mink: Comparisons of Their Pluripotencies Mol. Reprod. Deve., 36:148–158 (1993).

Talbot, et al. Culturing The EpiBlast Cells Of The Pig Blastocyst In Vitro Cell. Dev. Bio., 29(A):543–554 (1993).

Thomson, J., et al. Nonsurgical uterine stage preimplantation embryo collection from the common marmoset J. Med. Primatol., 23:333–336 (1994).

Thomson, James A., et al. Pluripotent Cell Lines Derived from Common Marmoset (*Callithrix jacchus*) Blastocysts. Biology of Reproduction, 55:254–259 (1996).

Ware, et al. Development Of Embryonic Stem Cell Lines From Farm Animals Biol. Reprod., 38(Suppl. 1):129 (1988).

Thomson et al. Embryonic Stem Cell Lines Derived from Human Blastocysts. Science, vol. 282, pp. 1145–1147, Nov. 6, 1998.

Cruz et al. Origin of Embryonic and Extraembryonic Cell Lineages in Mammalian Embryos. Current Communications, vol. 4, pp. 147–204, 1991.

Nichols et al. Establishment of germ–line–competent embryonic stem (ES) cells using differentiation inhibiting activity. Development, vol. 110, pp. 1341–1348, 1990.

Thomson J. et al., Embryonic Stem Cell Lines Derived From Human Blastocysts. Science, 282: 1145–1147 (1998).

* cited by examiner

COMPOSITE BLASTOCYSTS (CBS) FROM AGGREGATES OF DISSOCIATED CELLS OF NON-VIABLE PRE-EMBRYOS

BACKGROUND—FIELD OF INVENTION

In general, the field of the present invention is blastocysts. Specifically, the field of the present invention is composite blastocysts formed following dissociation, selection, and aggregation of cells derived from discarded pre-embryos.

BACKGROUND—DESCRIPTION OF PRIOR ART

During therapeutic in vitro fertilization, several eggs (15 on average) are collected from the female patient's ovaries following stimulation by exogenous gonadotrophins. Following retrieval, the eggs are incubated for 4–6 hours then inseminated with sperm obtained from the male partner. Approximately 16 hours following the insemination procedure, eggs are checked for evidence of fertilization; fertilization is confirmed when two pronuclei, one originating from each gamete donor, are visualized in the egg. At this stage, the entity is a single cell called a zygote. The zygote is then cultured for an additional two days during which it typically undergoes three cleavage divisions, yielding an eight-cell pre-embryo. It is typically at this stage of development that pre-embryos are replaced into the uterine cavity in hopes of establishing a pregnancy. Approximately 25% of the replaced pre-embryos develop into a fetus. Pre-embryos that are not replaced are frozen, for later therapeutic use, if they are normal in morphology or (in case of preimplantation genetic diagnosis) cytogenetically. If they are morphologically or cytogenetically abnormal, they are considered non-viable and are therefore discarded.

A multitude of studies over the past two decades have identified cleavage rate, cell number, cleavage symmetry, cytoplasmic fragmentation, blastomere nucleation, zona pellucida structure, degree of cell-cell contact, and cytoplasmic organization as key markers of viability in fresh human pre-embryos. The viability of frozen-thawed cleavage stage pre-embryos is judged, in addition, by the proportion of cells that remain intact after thawing.

Development is severely compromised in fresh or frozen/thawed pre-embryos with the following characteristics, singly or in combination: 1) Fewer than 2 cells on day 2 of development; 2) Fewer than 5 cells on day 3 of development; 3) No division in 24 hours of culture; 4) One or more highly uneven cleavage divisions; 5) Loss of 35% or more of total cytoplasmic volume to fragmentation or degeneration; 6) Large fragments distributed throughout the pre-embryo, 7) One or more multinucleated blastomeres appearing either on day 2 or day 3 of development; 8) Less than 50% of the cells intact after thawing of cryopreserved pre-embryos (Fresh pre-embryo morphology is reviewed by Alikani et al., Human Embryo Morphology and Developmental Capacity, In: *Mammalian Embryo Quality Evaluation, Invasive and Non-invasive Techniques*, Ann Van Soom and Marlene Bjorn, eds., Kluwer's Academic Publishers, 2002, in press; Frozen-thawed pre-embryo development capacity is analyzed by Edgar D H et al., A quantitative analysis of the impact of cryopreservation on the implantation potential of human early cleavage stage embryos. Human Reproduction 15: 175–179, 2000).

Blastocysts typically develop on the fifth or sixth day of pre-embryo culture in vitro. At this time, they typically contain from 50 to over 100 cells. A blastocyst is composed of two tissue types 1) a distinct inner cell mass (ICM) placed eccentrically in the blastocoelic cavity, and a single-cell layer of enclosing trophectoderm (TE). Cells of the ICM and TE can be differentially stained using bisbenzimide and propidium iodide, respectively (Thouas et al., Simplified technique for differential staining of inner cell mass and trophectoderm cells of mouse and bovine blastocysts, Reproductive Bio Medicine On Line; web paper, Vol. 3, No. 1, 25–29, 2001). While 70% of eggs fertilized in-vitro typically undergo the first three cleavage divisions during three days in culture, less than 50% advance to cavitation after five days (Gardner et al., A prospective randomized trial of blastocyst culture and transfer in in-vitro fertilization. Human Reproduction, 13:3434–3440, 1998), and about one third of those blastulating form morphologically normal blastocysts that expand to fill the zona pellucida completely and have a well defined ICM, and a cohesive TE. Pre-embryos with the abnormalities mentioned above hardly ever form blastcysts even under optimal culture conditions (Alikani et al., Cleavage anomalies in early human embryos and survival after prolonged culture in vitro, Human Reproduction, 15:2634–2643, 2000). These abnormal pre-embryos are therefore discarded.

One patent referring to blastocysts, U.S. Pat. No. 5,541,081, discusses the use of biochemical markers. The use of blastocysts for deriving embryonic stem (ES) cells is discussed in U.S. Pat. Nos. 5,843,780, 6,200,806, 628,971 which are incorporated by reference.

In some mammals, composite blastocysts (CBs) have been produced experimentally by combining two or more whole embryos or cells derived from two or more embryos (McLaren A and Bowman P. Mouse chimaeras derived from fusion of embryos differing by nine genetic factors. Nature 224:238–240; 1969)

The production and use of CBs from cells derived from normal embryos are discussed by Fehilly CB et al. (Interspecific chimaerism between sheep and goat, Nature 307: 634–636, 1984) and, Experimental chimaerism in sheep, J Reproduction and Fertility 70:347, 1984). No reference exists in the literature to either the production or the potential uses of CBs from non-viable, zygote-derived pre-embryos within a species.

CBs could be used to produce TE- and/or ICM-derived ES cells and cell lines. The latter have a vast number of clinical and scientific uses (NIH website on stem cells).

Present day embryo-based therapeutics and the state of the art clinical embryology pre-suppose the use of viable, potentially implantable pre-embryos. Pre-embryos with abnormal morphology are assumed by investigators of ordinary, as well as expert, skill in the art to have aberrant component cells (Jurisicova et al., Programmed cell death and human embryo fragmentation. Molecular Human Reproduction, 2: 93–98, 1996; Antczak and Van Blerkom, Temporal and spatial aspects of fragmentation in early human embryos: possible effects on developmental competence and association with the differential elimination of regulatory proteins from polarized domains. Human Reproduction, 14: 429–447, 1999).

Therefore the use of components from discarded abnormal pre-embryos is not obvious to those of ordinary, as well as expert, skill in the art. Nor has this approach been discussed at embryology conferences or published or patented. This invention, therefore, is novel and in addition represents a paradigm shift in the area of embryology.

BRIEF SUMMARY OF THE INVENTION

This invention is a product and a process. The product is a composite blastocyst (CB). The process is an aggregation process (AP). The material for both the process and the product is non-viable discarded pre-embryos. The CB is characterized by a cellular morphology having two distinct tissue types, the inner cell mass (ICM) stainable with bisbenzimide, and the trophectoderm (TE) stainable with propidium iodide, and a blastocoelic cavity (BC). The ICM contains embryonic stem (ES) cells, which are pluripotent. The primate TE is characterized by the production of chorionic gonadotrophin. The method of making CBs is an AP comprising inter alia the following steps: 1) dissociation of non-viable discarded pre-embryos; 2) selection of single-nucleated cells from several dissociated discarded pre-embryos; 3) microsurgical placement of multiple cells within a host zona pellucida or artificial aggregation in a non-zona vessel; 5) primary culture of the aggregates for multiplication and differentiation of cells.

The CB can be used to make

I) ES cell lines. True ES cell lines are characterized as follows:

i) they are capable of indefinite proliferation in vitro in an undifferentiated state;

ii) they are capable of differentiation into derivatives of all three embryonic germ layers (endoderm, mesoderm, and ectoderm) even after prolonged culture;

iii) they maintain a normal karyotype throughout prolonged culture. The true primate ES cell lines are therefore pluripotent.

II) TE derived stem (TES) cells.

Historically, the production of ES and TES cells has required the use of viable pre-embryos and their maintenance in culture until the development of a blastocyst containing an ICM and a TE. The source of viable human pre-embryos has been either unwanted frozen embryos donated to research by couples who have already undergone an IVF treatment cycle (Thomson et al. Embryonic stem cell lines derived from human blastocysts, Science 282:1145–1147,1998) or embryos created specifically for the purpose of stem cell production using gamete donors (Lanzendorf et al., Use of human gametes obtained from anonymous donors for the production of human embryonic stem cell lines. Fertility and Sterility 76: 132–137, 2001). Neither of these options is regarded acceptable by the federal government of the United States since they involve the destruction of viable pre-embryos; human embryonic stem cell research is therefore not federally funded unless the cell lines were made prior to Aug. 9, 2001(Fletcher L. US Stem cell policy comes under fire. Nature Biotechnology, 19: 893–894, 2001).

The present invention provides an alternative to the use of viable pre-embryos for these purposes, that is, the use of non-viable pre-embryos.

Three lines of evidence have led us to this invention:

1) each component cell within a normal mammalian embryo was found to maintain its totipotency at least through the first three cleavage divisions (Tarkowski A K and Wroblewska J. Development of blastomeres of mouse eggs isolated at the 4- and 8-cell stage, J Embryology and Experimental Morphology, 18(1):155–80,1967; Willadsen S M and Polge C, Attempts to produce monozygotic quadruplets in cattle by blastomere separation. Veterinary Record 108:211–3, 1981; Willadsen S M, The development capacity of blastomeres from 4- and 8-cell sheep embryos, J Embryology and Experimental Morphology 65:165–172, 1981; Willadsen S M, The viability of early cleavage stages containing half the normal number of blastomeres in the sheep. J Reproduction and Fertility, 59: 357–62, 1980)

2) chimeric embryos produced from normal cells isolated from viable embryos were capable of full development (Fehilly C B et al., Experimental chimaerism in sheep, J Reproduction and Fertility 70:347, 1984)

3) while non-viable discarded pre-embryos either arrest in extended culture or undergo abnormal development (Alikani et al., Cleavage anomalies in early human embryos and survival after prolonged culture in vitro, Human Reproduction, 15:2634–2643, 2000), a large proportion of component cells from such non-viable pre-embryos undergo one or two divisions and proceed to cavitation when cultured in isolation (Alikani, unpublished observations).

OBJECTS AND ADVANTAGES

The present invention is also summarized in that CBs are morphologically similar to ordinary blastocysts. The CBs have a morphologically identifiable inner cell mass (ICM) and trophectoderm (TE). It is an advantageous feature of the present invention that the CB mimics the ordinary blastocyst in terms of its complex morphological development. Therefore, the present invention inter alia allows cells from discarded pre-embryos to serve as a source of human embryonic and trophectodermic stem cells without the need to create new pre-embryos or destroy any existing viable pre-embryos.

It is an object of the invention to provide the material for producing primate ES cell lines without creation of new embryos or destruction of existing viable and/or implantable embryos.

It is an object of the invention to provide a primate CB that can be the material for creating ES cells without creation of new embryos or destruction of viable and/or implantable embryos.

It is another object of the present invention to provide the material for producing primate embryonic stem cell lines wherein the cells differentiate into cells derived from mesoderm, endoderm, and ectoderm germ layers without creation of new embryos or destruction of viable embryos.

Other objects, features, and advantages of the present invention will become obvious after study of the specification, drawings, and claims.

BRIEF DESCRIPTION OF THE DRAWINGS (37CFR1.84b(1) allows for black and white photomicrographs of histological tissue cross sections either stained or unstained. The figures below are such.)

FIG. 1 is a photomicrograph illustrating a morphologically normal day 3 pre-embryo.

FIGS. 2A-D is a set of photomicrographs of non-viable pre-embryos.

Photomicrograph 2A demonstrates (a degree of) blastomere fragmentation denoting non-viability in a day 3 pre-embryo.

Photomicrograph 2B demonstrates blastomere multinucleation in a day 2 pre-embryo denoting non-viability.

Photomicrograph 2C demonstrates grossly uneven cell division in a day 3 pre-embryo denoting non-viability.

Photomicrograph 2D demonstrates a day 1 zygote with maternal and paternal pronuclei grossly unequal in size, denoting high risk for genetic abnormality, hence non-viability.

Figure 3:
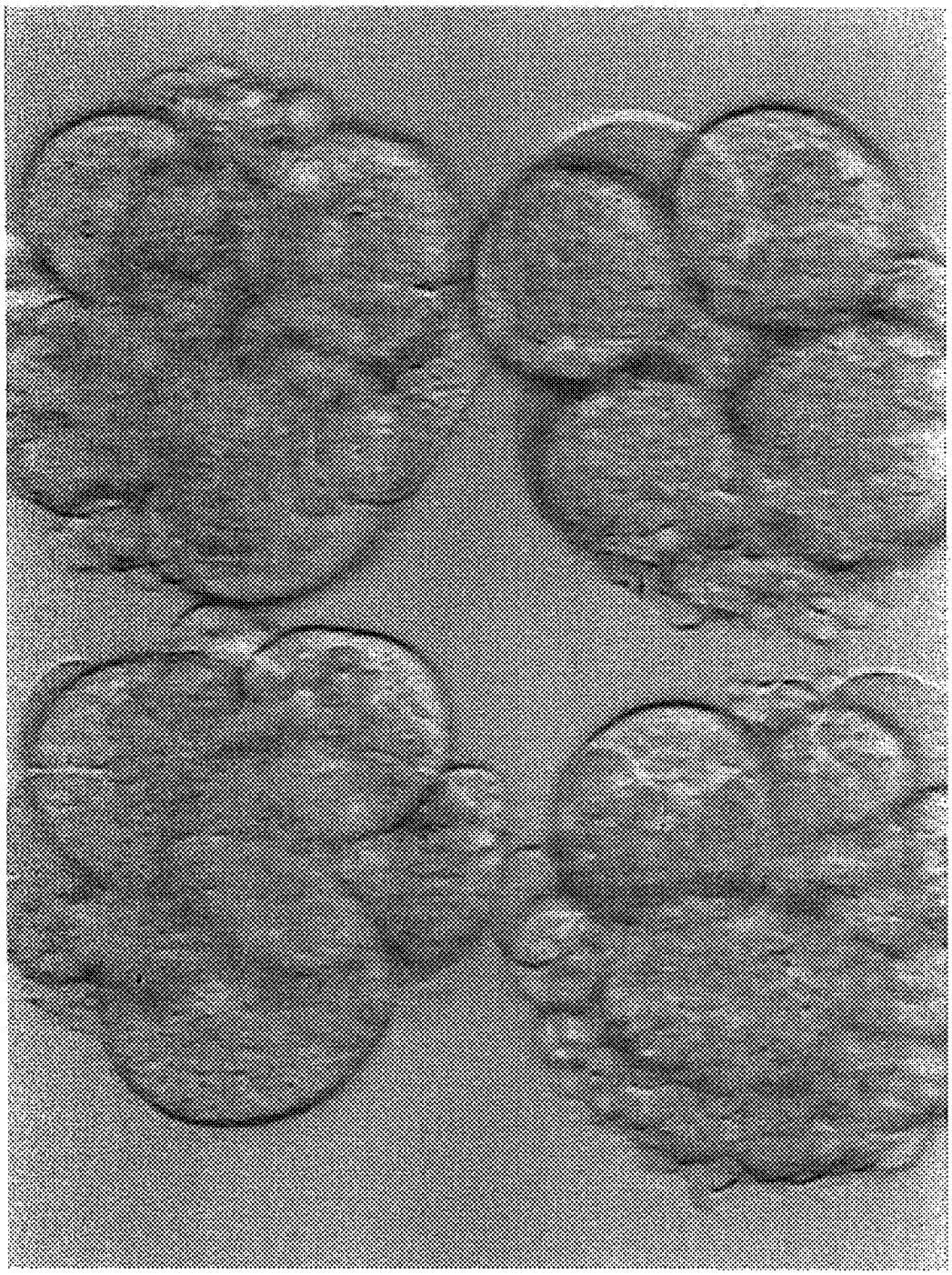

FIG. 3 is a photomicrograph illustrating four morphologically abnormal embryos, after zona pellucida removal, before dissociation.

Figure 4:

FIG. 4 is a photomicrograph of selected dissociated, nucleated cells of abnormal pre-embryos in FIG. 3, aggregated in two host zonae pellucidae (U.S. Pat. No. 6,132,952 Cohen et al.)

Figure 5:

FIG. 5 is a photomicrograph of two CBs that developed from continued culture of the zona-encapsulated aggregates shown in FIG. 4.

DETAILED DESCRIPTION OF THE PREFERRED EMBODIMENTS

Materials and Methods

Equipment, culture media, tools, and zona pellucida preparation were as described in U.S. Pat. No. 6,132,952, incorporated by reference, with modifications as described below.

All micromanipulations were performed in HEPES buffered human serum albumin-supplemented Human Tubal Fluid (MM). Micromanipulation was performed in shallow Falcon 1006 dishes using 20 microliter droplets of MM. All micromanipulation was performed at 37 degrees centigrade. The procedures were performed at 40× magnification using an IX-70 inverted Olympus microscope equipped with Hoffman interference optics and connected to a 14-inch monitor. The microtools were made according to known techniques.

Patients undergoing egg retrieval, IVF and embryo transfer consented to donate discarded pre-embryos. In total, fifty-one discarded pre-embryos were used. A total of 218 cells were isolated (average 4.27 cells per embryo), 57 of which were selected. Fifteen zona-encapsulated cell aggregates were produced, of which four developed into CBs (FIG. 5).

Source and Preparation of Empty Zonae Pellucidae (ZP)

Empty ZP were obtained from available sources, including:

i) pre-fertilization discarded immature oocytes ii) post-fertilization embryos, with abnormal fertilization or development.

Holes in the ZP were made mechanically or by laser irradiation.

Cytoplasm was extracted using a 30 micrometer (outer diameter) micropipette controlled by an air-filled syringe. The ZP was positioned so that the incision was situated at the three o'clock position. The microtool was inserted through the aperture, moved through the oolemma, and the cytoplasm was fully aspirated until the ZP was empty.

Method for Production of CBs

Method for ZP Removal and Dissociation of Discarded Pre-Embryos

Discarded pre-embryos were collected upon completion of the patients' treatment cycle, i.e., post replacement and cryopreservation of viable pre-embryos (FIG. 1) on the afternoon of day 3 in culture. Discarded pre-embryos (see examples in FIGS. 2A–D) were placed in a solution of 0.1% pronase at 37° C. for about one minute. They were then transferred to a fresh drop of MM using a hand-drawn, fire-polished, Pasteur pipette with a tip diameter slightly larger than the diameter of the ZP. Each pre-embryo was aspirated into and expelled from the pipette several times in order to mechanically remove the remnants of the dissolving ZP. Once the ZP remnants were removed, the pre-embryos were washed in fresh MM in order to remove any trace of pronase (FIG. 3). The pre-embryos were then placed in MM without calcium and magnesium for about five minutes and dissociated mechanically, using a pipette with an outer diameter of 80 micrometers, by repeated aspiration and expulsion. In this way, nucleated cells and anucleate fragments of cells were isolated.

Method for Aggregation of Cells from Several Discarded Pre-Embryos

Empty ZP and dissociated cells with a single nucleus were transferred to an MM droplet in a 1006 Falcon dish. The dish was placed on the stage of an inverted microscope equipped with hydraulic micromanipulators. A holding pipette, attached to the left micromanipulator, was used to hold the ZP in place, with the opening between the 3 and 5 o'clock positions. A biopsy needle with an outer diameter of 40 micrometers, attached to the right micromanipulator, was used to pick up nucleated cells. Anucleate Fragments were not used. Four to nine nucleated cells were inserted, one cell at a time, into the ZP (through the opening). The zona-encapsulated cell aggregate (FIG. 4) was then released from the holding pipette, transferred to fresh medium and cultured at 37° C. in an atmosphere of 5% $CO_2$ and 100% humidity. Culture was continued (typically for two days) until a composite blastocyst developed (FIG. 5).

We claim:

1. A method of producing composite blastocysts comprising:

a) dissociation of non-viable mammalian pre-blastocyst embryos into non-nucleated and individual nucleated cells or groups of cells;

b) isolation of individual mononucleated cells or groups of mononucleated cells from disaggregated non-viable pre-blastocyst embryos;

c) aggregation of isolated mononucleated cells or groups of mononucleated cells from non-viable pre-blastocyst embryos in a host zona pellucida; and d) culturing of the zona-encapsulated cell aggregates to allow multiplication of cells to form a composite blastocyst.

* * * * *